United States Patent [19]
Tu

[11] Patent Number: 5,893,884
[45] Date of Patent: *Apr. 13, 1999

[54] CATHETER SYSTEM HAVING ROLLABLE ELECTRODE MEANS

[75] Inventor: Hosheng Tu, Tustin, Calif.

[73] Assignee: Irvine Biomedical, Inc., Irvine, Calif.

[*] Notice: This patent is subject to a terminal disclaimer.

[21] Appl. No.: 08/997,041

[22] Filed: Dec. 23, 1997

Related U.S. Application Data

[63] Continuation of application No. 08/858,736, May 19, 1997, and a continuation of application No. 08/867,469, Jun. 2, 1997.

[51] Int. Cl.[6] ............................................. A61N 1/06
[52] U.S. Cl. ............................................. 607/120; 606/41
[58] Field of Search ................................. 607/119, 120, 607/121, 154, 122, 101; 606/29, 41

[56] References Cited

U.S. PATENT DOCUMENTS

| | | | |
|---|---|---|---|
| 5,242,441 | 9/1993 | Avitall | 606/41 |
| 5,643,255 | 7/1997 | Organ | 606/41 |

*Primary Examiner*—Scott M. Getzow

[57] ABSTRACT

An improved catheter system, having at least one rollable electrode at its tip section, can be used in ablating the arrhythmogenic point of a patient. A catheter suitable for radiofrequency ablation of cardiac tissues comprises a catheter shaft having a distal section, a distal end, a proximal end, and at least one lumen extending therebetween, wherein at least a rollable electrode is disposed at the tip section of the said catheter. In one embodiment, the ablation catheter has a temperature sensor and a close-loop temperature control mechanism. In another embodiment, the ablation catheter has fluid infusion and irrigation means at its distal tip section for creating a deep and large lesion by applying radiofrequency energy and cooled fluid to the said electrode.

20 Claims, 8 Drawing Sheets

CATHETER SYSTEM HAVING ROLLABLE ELECTRODE MEANS

RELATIONSHIP TO COPENDING APPLICATION

This application is a continuation of application Ser. No. 08/858,736, filed on May 19, 1997, and application Ser. No. 08/867,469, filed on Jun. 2, 1997 both pending; the entire contents of which are incorporated herein by reference.

FIELD OF THE INVENTION

The present invention generally relates to improved constructions for a catheter system. More particularly, this invention relates to catheters and methods for ablating cardiac tissues via a steerable ablation catheter having a rollable electrode at its tip section with fluid infusion and irrigation capabilities for ablating intracardiac tissues, resulting in a deeper and larger lesion in the cardiac tissue of the heart.

BACKGROUND OF THE INVENTION

Symptoms of abnormal heart rhythms are generally referred to as cardiac arrhythmias, with an abnormally rapid rhythm being referred to as a tachycardia. The present invention is concerned with the treatment of tachycardias which are frequently caused by the presence of an "arrhythmogenic site" or "accessory atrioventricular pathway" close to the inner surface of the chambers of a heart. The heart includes a number of normal pathways which are responsible for the propagation of electrical signals from the upper to lower chambers necessary for performing normal systole and diastole function. The presence of an arrhythmogenic site or an accessory pathway can either bypass or short circuit the normal pathway, potentially resulting in very rapid heart contractions, referred to here as tachycardias.

Treatment of tachycardias may be accomplished by-a variety of approaches, including drugs, surgery, implantable pacemakers/defibrillators, and catheter ablation. While drugs may be the treatment of choice for many patients, they only mask the symptoms and do not cure the underlying causes. Implantable devices only correct the arrhythmia after it occurs. Surgical and catheter-based treatments, in contrast, will actually cure the problem, usually by ablating the abnormal arrhythmogenic tissue or accessory pathway responsible for the tachycardia. It is important for a physician to accurately steer the catheter to the exact site for ablation. Once at the site, it is important for a physician to be able to control the emission of the energy dispersed, to ablate the tissue within the heart.

The particular interest of the present invention are radiofrequency (RF) ablation protocols, which have been proven to be highly effective when used by electrophysiologists for the treatment of tachycardia, by neurosurgeons for the treatment of Parkinson's disease, and also by neurosurgeons and anesthetists for other RF procedures such as Gasserian ganglionectomy for trigeminal neuralgia and percutaneous cervical cordotomy for intractable pains, while exposing a patient to minimal side effects and risks. Radiofrequency catheter ablation is generally performed after conducting an initial mapping study, where the locations of the arrhythmogenic site and/or accessory pathway are determined. After a mapping study, an ablation catheter is usually introduced to the target heart chamber and is manipulated so that the ablation tip electrode lies exactly at the target tissue site. Radiofrequency energy, or other suitable energy, is then applied through the tip electrode to the targeted cardiac tissue, in order to ablate the tissue of arrhythmogenic site or the accessory pathway. By successfully destroying that tissue, the abnormal signal patterns responsible for the tachycardia may be eliminated.

The impedance usually rises at the tissue contact site when RF energy is delivered through an electrode. To create a deeper and larger lesion, the surface of the tissue contact sites needs to maintain a proper temperature through the use of a cooled fluid irrigation or infusion to partially compensate for the temperature rise due to RF energy delivery. The following U.S. patents have disclosed the use of irrigation ports in different manners to cool the tissue contact surface. Those patents are U.S. Pat. No. 5,545,161 to Imran, U.S. Pat. No. 5,462,521 to Brucker et al., U.S. Pat. No. 5,437,662 to Nardella, U.S. Pat. No. 5,423,811 to Imran et al., U.S. Pat. No. 5,348,554 to Imran et al., and U.S. Pat. No. 5,334,193 to Nardella. In practice, the fluid coming out of the irrigation ports may not evenly cover all the surface area of the electrode or the tissue to be ablated. Furthermore, none of the above patents discloses an irrigation system of cooled fluid through a rotatable electrode means to form a uniform protective fluid layer around the electrode.

The tip section of a catheter is referred to herein as the portion of that catheter shaft containing at least one electrode. In one embodiment, a catheter utilized in the endocardial radiofrequency ablation is inserted into a major vein or artery, usually in the neck or groin area. The catheter is then guided into an appropriate chamber of the heart by an appropriate manipulation through the vein or artery. The tip of the catheter must be manipulatable by a physician from the proximal end of the catheter, so that the electrodes at the tip section can be positioned against the tissue site to be ablated. The catheter must have a great deal of flexibility in order to follow the pathway of the major blood vessels into the heart. It must permit manipulation of the tip by a user even when the catheter body is in a curved or twisted configuration.

The tip section of a conventional electrophysiology catheter that is deflectable usually contains one large electrode about 4 mm in length or longer for ablation purposes. The lesion is generally not deep, because of the potential impedance rise of the tissue in contact with the "stationary" catheter electrode and thereafter, the ablation time needs to be cut short. The word "stationary" means that the contact point of the electrode, with any tissue, remains at the same point. In some cases, the contact of a stationary electrode of the conventional catheter with tissues, reportedly results in potential tissue adhering to the said electrode. A rollable electrode is needed to reduce the tissue contact impedance rise and the temperature rise by slightly moving the rollable electrode around in a micro-moving manner so that the temperature rise is decreased by the surrounding fluid, or by the cold irrigation fluid. Even in the case of a conventional catheter having irrigation capabilities by utilizing an irrigation port, the cooled fluid does not evenly and uniformly rinse the electrode, because the electrode is not rotatable or rollable, and the constant contact point of a stationary electrode with a tissue prevents fresh cold fluid from coming into place.

Avitall in the U.S. Pat. No. 5,242,441, teaches a rotatable tip electrode. The said electrode is secured to a high torque wire for rotation and electrical conductivity. The tissue contact region is always the same unless the electrode is rotated by an external mechanism intermittently. The potential coagulum at the contact region due to impedance rise does not go away because of the relatively stationary position of the rotatable tip electrode and the absence of fluid irrigation.

Organ in the U.S. Pat. No. 5,643,255, discloses a catheter whose tip electrode is axially rotatable. In both of the above-mentioned patents, the rotation of the tip electrode is accomplished by a manual rotating action externally, which is cumbersome. There is a need for a catheter which contains at least a rollable electrode by purely moving the catheter around.

While a radiofrequency electrophysiology ablation procedure using an existing catheter has had promising results, the tip section of a known catheter usually has a fixed non-rollable electrode and a fluid infusion port which may not evenly rinse the electrode when contacting the tissue for ablation purpose. Therefore there is a need for an improved catheter and methods for making a deeper and larger lesion in the cardiac tissue.

SUMMARY OF THE INVENTION

In general, it is an objective of the present invention to provide an improved catheter for even distribution of fluid infusion and irrigation. The capability of even fluid irrigation may be applicable to special means of cooling off the tissue contact site due to impedance rise as a result of RF ablation operation. It is another objective of the invention to provide an ablation catheter with a tip section having at least a rollable electrode. The rollable electrode consists of two general categories: first, the ones without a supporting stem, such as a ball electrode; and second, the ones with a supporting stem, such as a roller electrode, a wheel electrode, a circular saw electrode, and the like. Another objective of the invention is to provide a free rollable electrode which is to be used in effectively ablating the arrhythmogenic point of a patient. It is another objective of the invention to provide a rollable electrode constructed with a porous substrate.

This catheter is particularly useful for treating the patient with tachycardia because of its cooled electrode, which is obtained by applying fluid irrigation means. The fluid may be selected from the group of saline, heparin, antibiotics, chemotherapy and therapeutics fluids.

In one embodiment, an ablation catheter system comprises a catheter shaft having a distal tip section, a distal end, a proximal end and at least one lumen extending therebetween. A handle is attached to the proximal end of the said catheter shaft. A distal tip section of the catheter shaft, which is proximal to the distal end, comprises at least a hollow pocket, wherein a hollow pocket has a ball electrode inside it, and a lumen having fluid infusion and irrigation capabilities. In another embodiment, the tip section contains a rollable electrode, such as a roller electrode, a wheel electrode, or a circular saw electrode. The ball electrode is free to float, roll, or rotate within the pocket, wherein the shape of the ball is not limited to the round shape.

A fluid source is positioned at one end of the catheter for supplying a fluid flow through the lumen of the said catheter shaft to the tip section which has a rollable electrode. Therefore at ablation time, the tip section, with at least a rollable electrode, is positioned against the tissues to be ablated. The fluid is continuously or intermittently supplied through the lumen to evenly cover and rinse the electrode so that the impedance rise at the contact site is substantially reduced. Cooling off the electrode during RF energy delivery will result in optimal ablation efficiency and the desired deep and large lesion.

In a further embodiment, the catheter comprises a flat wire which is disposed inside the lumen of the catheter shaft. The proximal end of the said flat wire is secured to a deployment means on the handle of the said catheter system, and is further connected to a conducting wire, which is secured to a contact pin of the connector, which is secured at the proximal end of the handle. Therefrom, the conducting wire is connected to an external RF generator for the ablation operations using the ball electrode. The conducting wire is also connected to an EKG monitor for recording and displaying the endocardial electrical signal.

In one embodiment, a portion of the flat wire is substituted by a coil wire so that the properties of a spring are contained herein. The distal end of the flat wire is shaped as a receptive concave bowl or other appropriate shapes for contacting the said rollable electrode. The concave bowl comprises an appropriate radius as that of the rollable electrode, and contacts the surface of the electrode appropriately when the electrode is pressed inwardly during contact with the tissue. In an alternate embodiment, the distal end of the flat wire is equipped with a brush-like pick off mechanism for the circular saw type electrode to intimately contact the flat wire when the deployment means is deployed. The contact of the flat wire with the electrode enables the rollable electrode for mapping and/or ablation purpose. A flat wire deployment means on the handle can be deployed so that when the flat wire is pushed forward, the rollable electrode is forced to tightly position itself against the tip of the catheter shaft, wherein the tip is bent slightly inward to hold the rollable electrode. When the rollable electrode contacts the flat wire, the rollable electrode can be used as a mapping electrode for recording and displaying the endocardial electrical signal through the assistance of an external EKG monitor, and as an ablation electrode when in association with an external RF generator energy source. By intermittently contacting the flat wire to the rollable electrode, the contacting site of the electrode can be rotated and/or the fluid irrigation to the rollable electrode can be applied.

The ablation catheter further comprises a steering mechanism at the handle for controlling the deflection of the said distal tip section having fluid infusion and irrigation capabilities. Usually, a rotating ring or a push-pull plunger is employed in the steering mechanism. In another embodiment, the steerable ablation catheter comprises a bi-directional deflection, or multiple curves deflection of the tip section. One end of the steering wire is attached at a certain point of the tip section of the said catheter shaft. The other end is attached to the steering mechanism at the handle. The steering mechanism on the steerable catheter or device is well-known to those who are skilled in the art.

A fluid conveying lumen is associated with the elongated catheter shaft, and is preferably disposed within the catheter shaft along the longitudinal axis thereof. The lumen is adapted to communicate with a fluid supply source to convey fluid from the source, and through the lumen, to be discharged out of the tip section containing a fluid vent opening.

This invention also comprises a method and system for controlling the flow rate of fluid through the lumen to optimize the cooling effect of the energy delivering electrode of the catheter. The control system preferably regulates the flow rate, which is based on signals representative of the temperature of the catheter tip and/or tissue impedance.

In a particular embodiment, at least one other electrode is disposed at the tip section of the catheter shaft. One conducting wire which attaches to the said electrode, passes through the lumen of the catheter shaft and through the interior void of the handle, and is thereafter secured to a contact pin of the connector, which is secured at the proximal end of the handle. Therefrom, the conducting wire is connected to an external RF generator for ablation operations. The conducting wire is also connected to an EKG monitor for recording and displaying the endocardial or epicardial electrical signal.

In an additional embodiment, the ablation system further comprises a temperature sensing and a close-loop temperature control mechanism for the electrode, having at least one temperature sensor adjacent to the tissue contact site of the electrode. The location of the temperature sensor is preferably in the very proximity of one of the electrodes. In a still further embodiment, a method for operating an ablation catheter further comprises a programmed temperature control mechanism for independently controlling the delivery of the RF energy of each electrode of the ablation catheter.

It is another objective of the invention to provide a catheter system with a rollable electrode at the side of the tip section of the catheter shaft, instead of at the distal end of the said catheter shaft. In one embodiment, the said catheter system with the side rollable electrode comprises fluid irrigation capabilities. In another particular embodiment, the material for the electrodes may consist of conductive metals such as platinum, iridium, gold, silver, stainless steel, Nitinol, or an alloy of their mixtures. It is another objective of this invention to provide a rollable electrode constructed with a porous substrate.

A method for operating a steerable ablation catheter system having a rollable electrode at the tip section having fluid irrigation means, within a heart chamber, comprises of: percutaneously introducing the catheter system through a blood vessel to the heart chamber; deflecting the distal section of the catheter about a transverse axis to position the tip section with at least a rollable electrode near a target region on an interior wall of the heart chamber; intimately contacting the electrode with the intracardiac tissue; applying radiofrequency energy to the target location through the electrode; and cooling the electrode by releasing cooled fluid through the lumen at the said distal tip section.

The catheter system of the present invention has several significant advantages over other known catheters or ablation techniques. In particular, the evenly cooled, rollable electrode, that is constructed of a porous substrate, of a steerable ablation catheter of this invention may result in a deeper and larger lesion which is highly desirable in the treatment of tachycardia.

BRIEF DESCRIPTION OF THE DRAWINGS

Additional objectives and features of the present invention will become more apparent and the invention itself will be best understood from the following Detailed Description of the Exemplary Embodiments, when read with reference to the accompanying drawings.

DETAILED DESCRIPTION OF THE EXEMPLARY EMBODIMENTS

Figure 1:
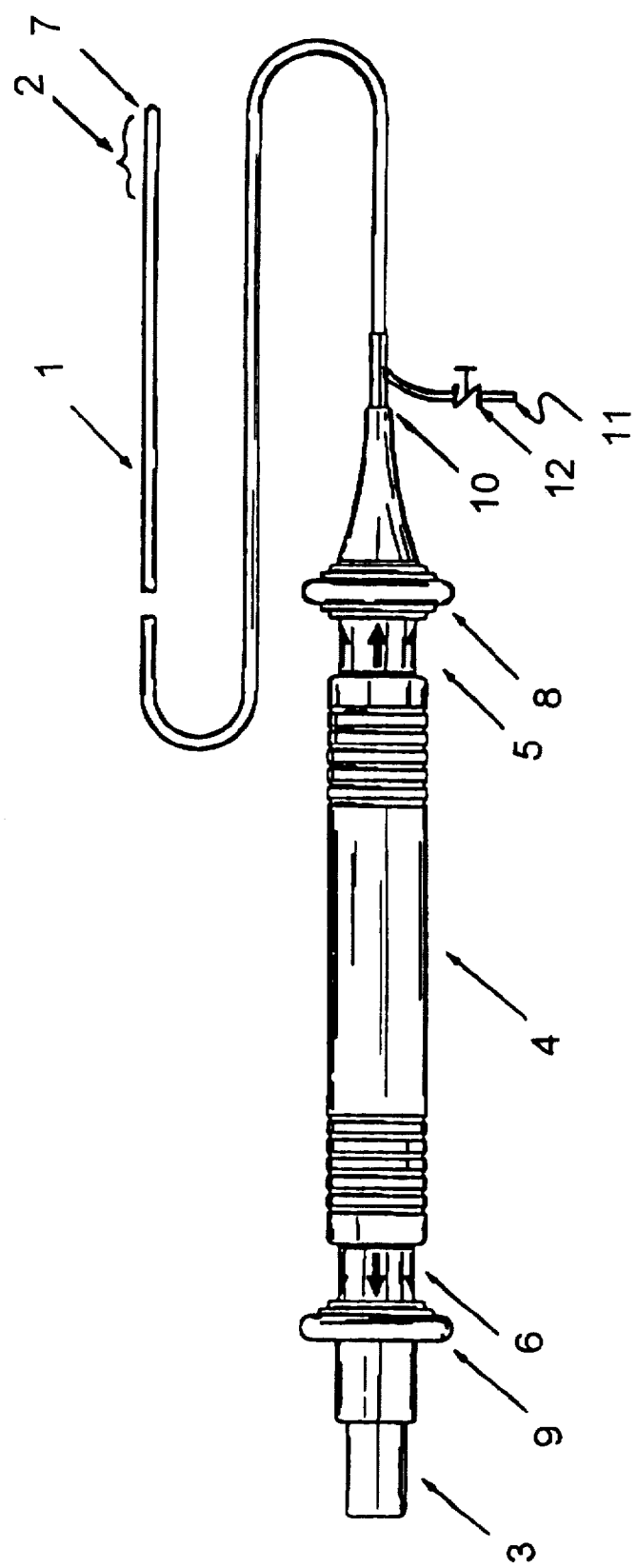
FIG. 1 is an overall view of the catheter system having a porous ball electrode at its distal tip section, constructed in accordance with the principles of the present invention.

FIG. 1 shows an overall view of the catheter system having a ball electrode with fluid infusion and irrigation means. A catheter system constructed in accordance with the principles of the present invention comprises: a catheter shaft 1 having a distal tip section 2, a distal end 7, a proximal end 10, and at least one lumen extending therebetween. The catheter system comprises a fluid infusion mechanism 11 close to the proximal end 10 of the catheter shaft 1. A control valve 12 is provided to the fluid infusion mechanism 11, which is externally connected to a fluid supply source having a pump and means (not shown) for controlling the flow rate of fluid through the lumen to optimize the cooling of the electrode of the catheter. A handle 4 is attached to the proximal end 10 of the said catheter shaft 1.

The connector 3 which is secured at the proximal end of the catheter system, is part of the handle section 4. The handle has at least one steering mechanism 5. The steering mechanism 5 is used to deflect the tip section 2 of the catheter shaft 1 for catheter maneuvering and positioning. In one embodiment, by pushing forward the front plunger 8 of the handle 4, the tip section of the catheter shaft deflects to one direction. By pulling back the front plunger 8, the tip section returns to its neutral position. In another embodiment, the steering mechanism 5 at the handle 4 comprises a means for providing a plurality of deflectable curves on the distal tip section 2 of the catheter shaft. In still another embodiment, the steering mechanism, by using rotatable means, can be used to substitute the push-pull means.

Figure 2:
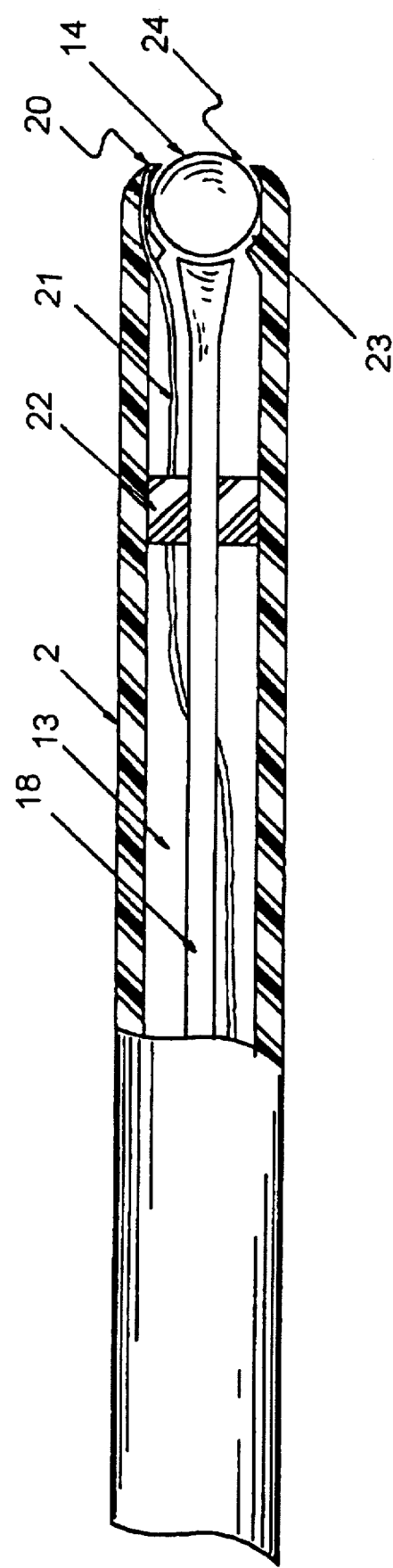
FIG. 2 is a close-up view of the distal section of the catheter system comprising a porous ball electrode at the distal end, having fluid infusion and irrigation capabilities.

FIG. 2 shows a close-up view of the distal section of the catheter system comprising of a porous ball electrode at the distal end, having fluid infusion and irrigation capabilities. In one embodiment, a fluid conveying lumen 13 is associated with the elongated catheter shaft 1, and is preferably disposed within the catheter shaft along the longitudinal axis thereof. The fluid conveying lumen is adapted to communicate with a fluid supply source (not shown) to convey fluid from the source and through the said lumen to be discharged out of the tip section 2 containing the ball electrode 14 and a vent opening 24.

Figure 3:
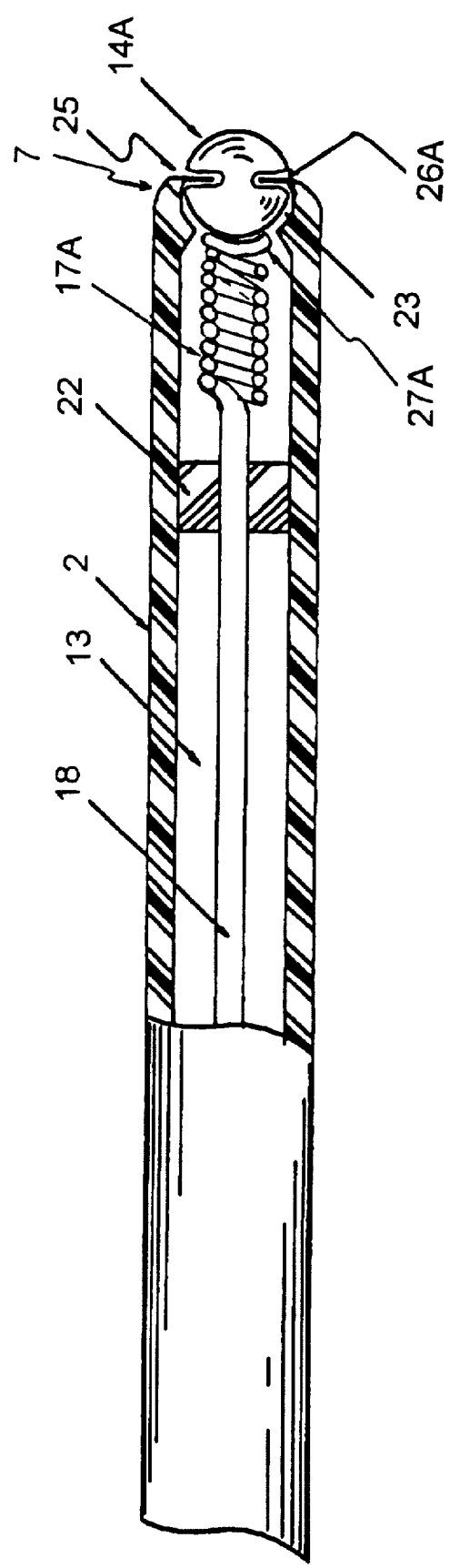
FIG. 3 is a close-up view of the distal section of the catheter system comprising a roller electrode at the distal end, having fluid infusion and irrigation capabilities.

FIG. 3 shows a close-up view of the distal section of an alternate catheter system comprising of a roller electrode at the distal end, having fluid infusion and irrigation capabilities. In one embodiment, the roller electrode 14A has two side holes and is suspended by the two support ears 26A which are extended from the tip 7 of the catheter shaft 1. In another embodiment, a through-hole 25 is created for the roller electrode 14A. A supporting stem which is secured at both sides to the tip 7 of the catheter shaft, passes within the through-hole 25. In either case, the two support ears, or the supporting stem, are made of conducting material and are connected to their respective conducting wires, which are externally connected to an EKG for diagnosis, or to an RF generator during an electrophysiology ablation procedure. Therefrom, the RF energy is transmitted through the conducting wire to the electrode and delivers the energy to the target tissue. In still another embodiment, a coil spring 17A is attached to the conducting wire 18 that is characteristically a flat wire. The distal receptacle end 27A of the coil spring is to contact the roller electrode 14A for RF energy delivery.

Figure 4:
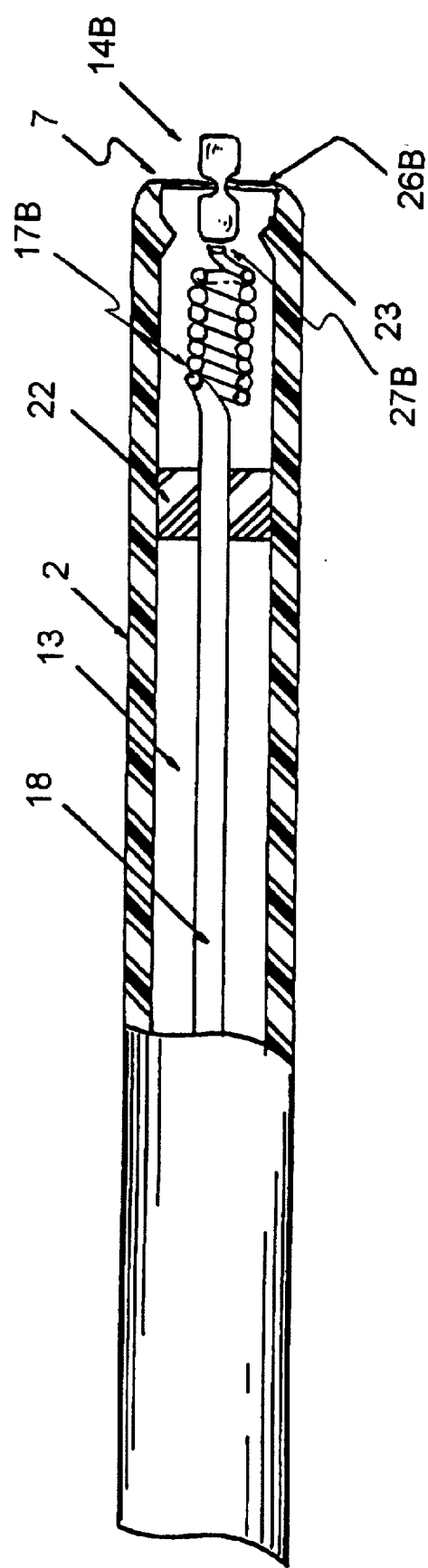
FIG. 4 is a close-up view of the distal section of the catheter system comprising a wheel electrode at the distal end, having fluid infusion and irrigation capabilities.

FIG. 4 shows a close-up view of the distal section of an alternate catheter system comprising of a wheel electrode 14B at the distal end, having fluid infusion and irrigation capabilities. In one embodiment, the wheel electrode 14B has a supporting stem 26B which is extended from the tip 7 of the catheter shaft 1 and passes through the wheel electrode. The supporting stem is made of conducting material and are connected to their respective conducting wires, which are externally connected to an EKG for diagnosis, or to an RF generator during an electrophysiology ablation procedure. Therefrom, the RF energy is transmitted through the conducting wire to the electrode and delivers the energy to the target tissue. In still another embodiment, a coil spring 17B is attached to the conducting wire 18 that is characteristically a flat wire. The distal receptacle end 27B of the coil spring is to contact the roller electrode 14B for RF energy delivery.

Figure 5:
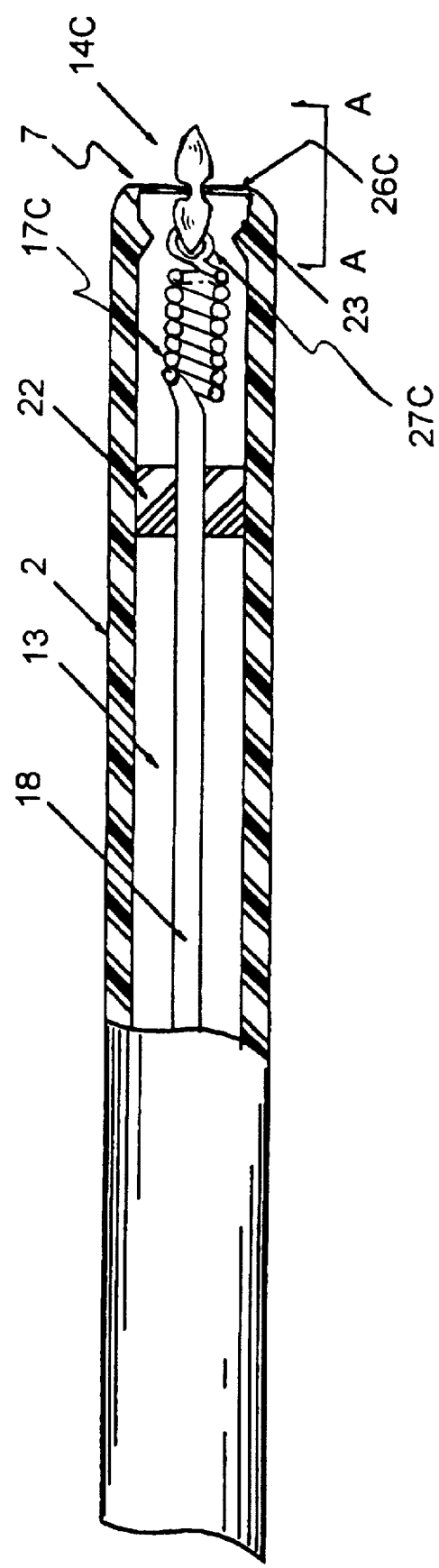
FIG. 5 is a close-up view of the distal section of the catheter system comprising a circular saw electrode at the distal end, having fluid infusion and irrigation capabilities.

FIG. 5 shows a close-up view of the distal section of an alternate catheter system comprising of a circular saw electrode 14C at the distal end, having fluid infusion and irrigation capabilities. In one embodiment, the circular saw electrode 14C has a supporting stem 26C, which is extended from the tip 7 of the catheter shaft 1, and passes through the circular saw electrode. The supporting stem is made of conducting material and is connected to their respective conducting wires, which are externally connected to an EKG for diagnosis, or to an RF generator during an electrophysiology ablation procedure. Therefrom, the RF energy is transmitted through the conducting wire to the electrode and delivers the energy to the target tissue. In still another embodiment, a coil spring 17C is attached to the conducting wire 18 that is characteristically a flat wire. The distal receptacle end of the flat wire means is equipped with a brush-like pick-off mechanism 27C for the circular saw electrode. The said brush-like pick-off mechanism is used for the conducting wire to contact the circular saw electrode 14C for RF energy delivery.

Figure 6:
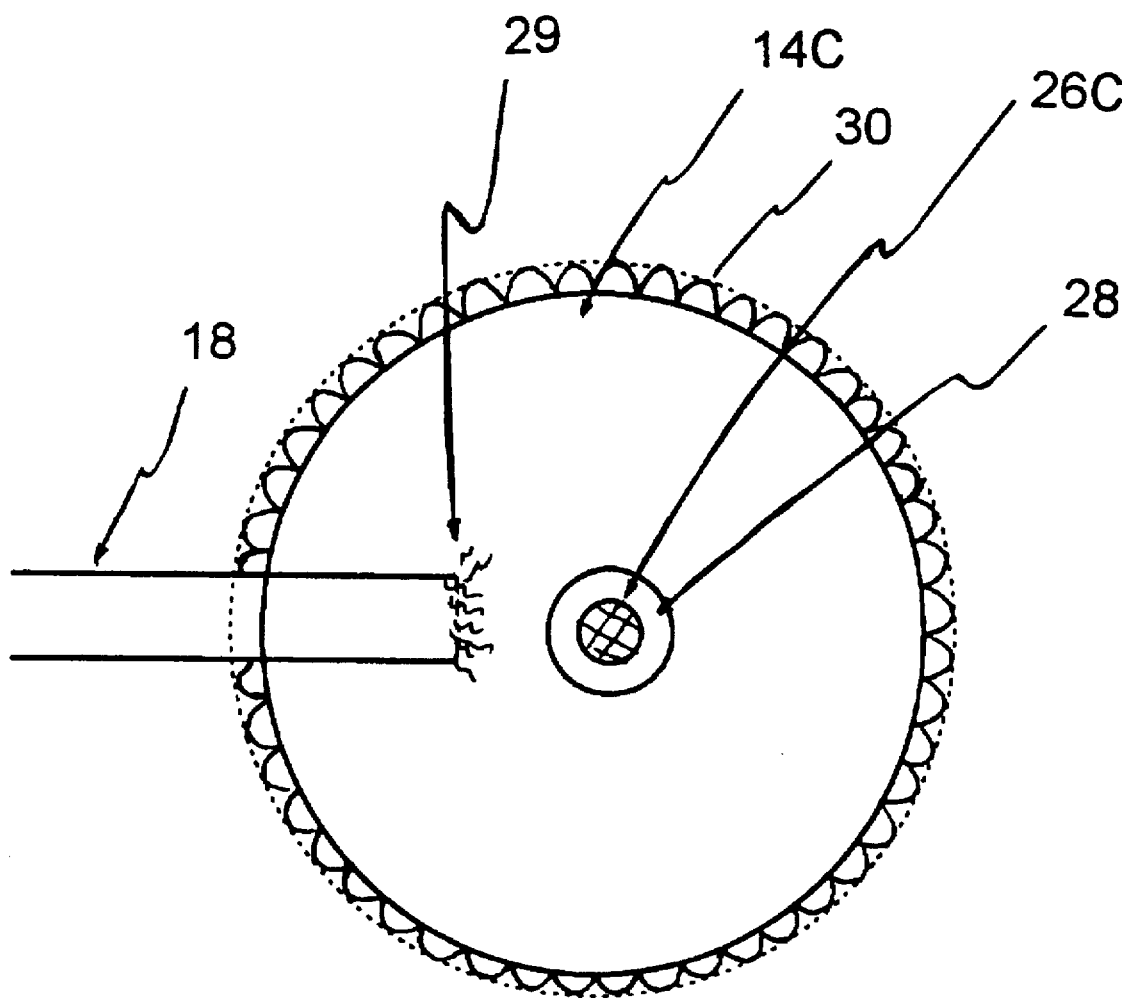
FIG. 6 is the A—A section of FIG. 5, showing the front view of a circular saw electrode.

FIG. 6 shows the A—A section of FIG. 5, that is the front view of a circular saw electrode 14C. The said electrode has a through-hole 28 where the supporting stem 26C passes through the said hole. The brush-like pick off mechanism 29 is secured to a portion of the flat wire 18. The teeth 30 of the circular saw electrode 14C can be either sharp or blunt.

Figure 7:
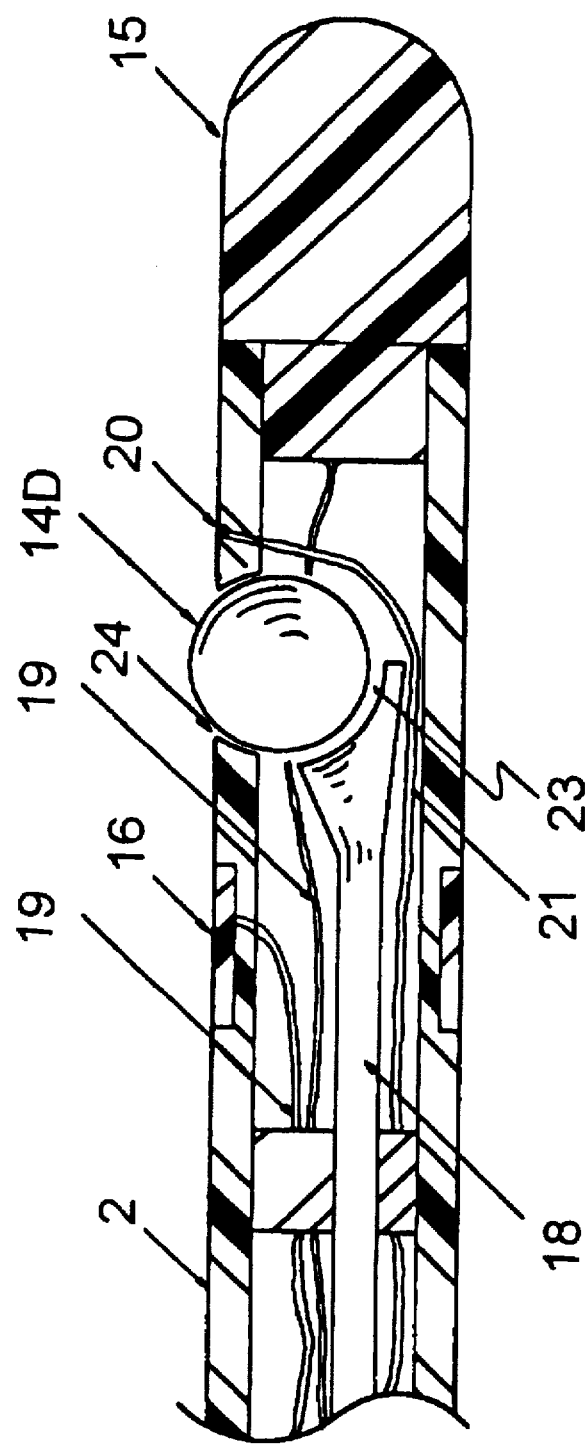
FIG. 7 is a close-up view of the distal section of an alternate catheter system comprising a porous ball electrode at one side of the tip section, having fluid infusion and irrigation capabilities.

FIG. 7 shows a close-up view of the distal section of an alternate catheter system comprising of a porous ball electrode 14D at one side of the tip section 2, having fluid infusion and irrigation means 11. The fluid flow rate from the fluid infusion mechanism 11 may approximately be between 5 ml/min. to 20 ml/min. In another embodiment, the tip section 2 of the catheter shaft 1 comprises a ball electrode 14D and at least one tip electrode 15 or a band electrode 16. The electrodes are formed of conducting materials selected from the group of platinum, iridium, gold, silver, stainless steel, and Nitinol.

Figure 8:
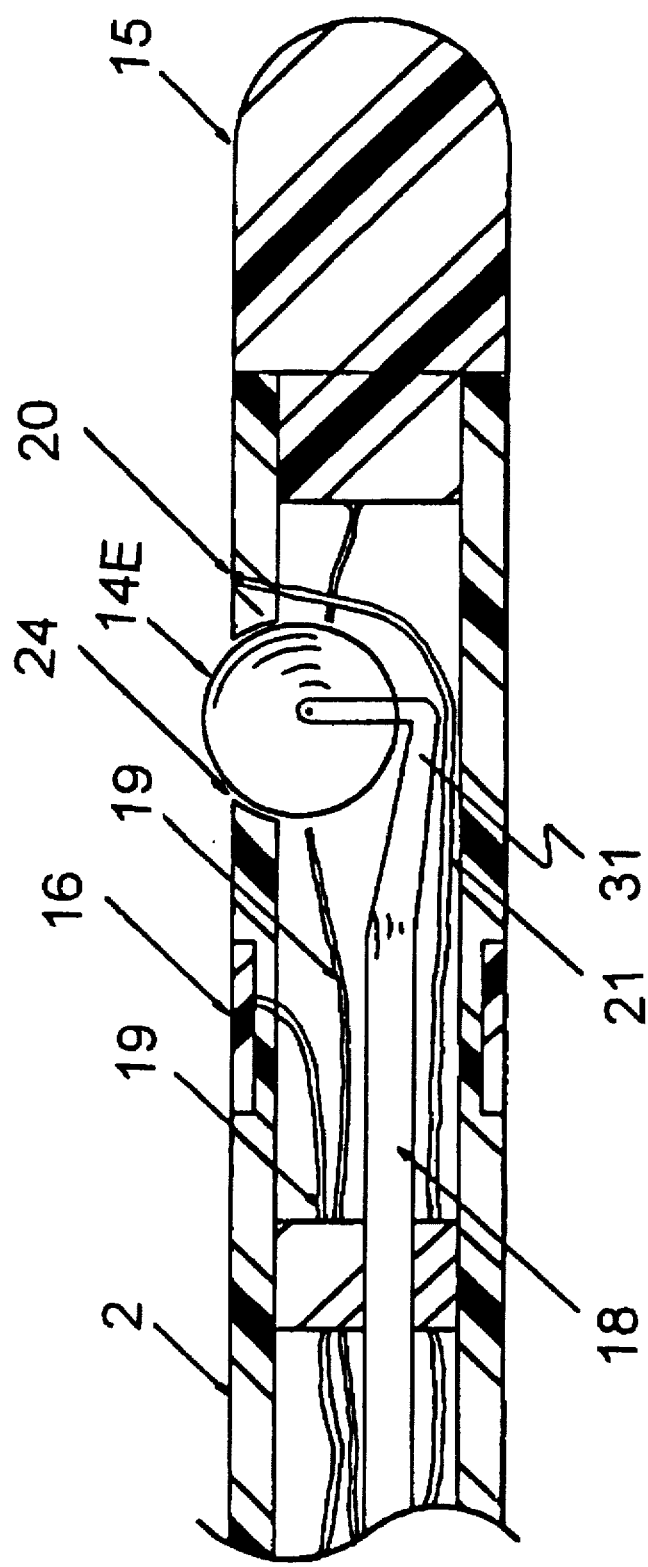
FIG. 8 is a close-up view of the distal section of an alternate catheter system comprising a rollable electrode at one side of the tip section, having fluid infusion and irrigation capabilities.

FIG. 8 shows a close-up view of the distal section of an alternate catheter system comprising a rollable electrode 14E at one side of the tip section 2, having fluid infusion and irrigation means 11. The rollable electrode is supported by a supporting stem 31, which is secured to a portion of the flat wire 18, that in turn, is part of the conducting wire of the present invention. The fluid flow rate from the fluid infusion mechanism 11 may approximately be between 5 ml/min. to 20 ml/min. In another embodiment, the tip section 2 of the catheter shaft 1 comprises a rollable electrode 14E and one tip electrode 15 or at least a band electrode 16.

The catheter system comprises a flat wire 18 which is disposed inside the lumen of the catheter shaft 1. The proximal end of the said flat wire is secured to a deployment means 6 on the handle 4 of the said catheter system, and is further connected to a conducting wire, which is soldered to a contact pin of the connector 3. The deployment of the tip section can be accomplished by pushing or pulling the plunger 9 of the deployment means 6. At least one electrode 15 or 16, has an insulated conducting wire 19 secured to the electrode, which passes through the lumen of the catheter shaft 1 and is secured to a contact pin of the connector 3 at the proximal end of the handle 4. The conducting wire from the connector end is externally connected to an EKG for diagnosis, or to an RF generator during an electrophysiology ablation procedure. Therefrom, the RF energy is transmitted through the conducting wire to the electrode and delivers the energy to the target tissue.

A temperature sensor 20, either by a thermocouple means or a thermister means, is constructed at the proximity of the electrodes 14A–14E, 15, or 16 is used to measure the tissue contact temperature when RF energy is delivered. The temperature sensing wire 21 from the thermocouple or thermister is connected to one of the contact pins (not shown) of the connector 3 and externally connected to a transducer and to a temperature controller. The temperature reading is thereafter relayed to a close-loop control mechanism to adjust the RF energy output. The RF energy delivered is thus controlled by the temperature sensor reading or by a pre-programmed control algorithm.

The catheter of this invention is also used to provide fluid communication and to commensurate flow of fluid originating inside the tip section of the catheter shaft, to the electrode exterior surface, which directs the fluid flow from inside the catheter shaft, over the exterior surface of the electrode to provide a fluid protective layer surrounding the electrode to minimize temperature elevation of the electrode with the biological tissues. This fluid protective layer surrounding the ball electrode is better maintained when the rollable electrode is freely rotatable or rollable. The construction material for any of the above-mentioned electrode can be a porous substrate.

To prevent blood or body fluid from backflowing into the proximal end of the fluid conveying duct 13, a silicone type check valve 22 is installed at certain opening of the lumen of the fluid conveying duct 13. The fluid conveying duct 13 is further extended all the way to the distal end. In one embodiment as shown in FIG. 2, the fluid conveying duct is extended to the hollow pocket 23 where a porous ball electrode 14 is disposed on the distal tip section 2 of the catheter shaft 1 and has a vent opening 24 facing the outside of the catheter shaft.

From the foregoing, it should now be appreciated that an improved catheter system, having a rollable electrode and a fluid infusion and irrigation capability, has been disclosed for ablation procedures, including endocardial, epicardial, or body tissue and drug delivery operations for tumor or cancer management. While this invention has been described with reference to a specific embodiment, the description is illustrative of the invention and is not to be construed as limiting the invention. Various modifications and applications may occur to those skilled in the art without departing from the true spirit and scope of the invention as described by the appended claims.

What is claimed is:

1. A catheter system comprising:

a catheter shaft having a distal tip section, a distal end, a proximal end, and at least one lumen extending therebetween, wherein the distal tip section has at least a hollow pocket;

a handle attached to the proximal end of the catheter shaft; and at least a ball disposed inside the said hollow pocket, wherein said ball is comprised of a porous substrate.

2. The catheter system as in claim 1, further comprising at least a conducting wire disposed inside the lumen, wherein said conducting wire is to contact the porous ball.

3. The catheter system as in claim 2, further comprising fluid being supplied to the distal tip section of the catheter shaft and disposed out of the hollow pocket having a porous ball electrode.

4. The catheter system as in claim 3, wherein the fluid is selected from the group of saline, heparin, antibiotics, chemotherapy and therapeutics fluids.

5. The catheter system as in claim 1, further comprising a steering mechanism at the handle for controlling the deflection of the distal tip section of said catheter system.

6. The catheter system as in claim 3, wherein the at least one hollow pocket is located at a side of the distal tip section of the catheter shaft.

7. The catheter system as in claim 2, further comprising RF energy being delivered to said at least one ball electrode disposed at the distal tip section.

8. The catheter system as in claim 7, further comprising at least one temperature sensing means at the distal tip section and a close-loop temperature control mechanism for the catheter system.

9. The catheter system as in claim 8, further comprising a means for controlling the flow rate of fluid through the lumen to optimize cooling of the electrode of the catheter, wherein the control system preferably regulates the flow rate based on signals from the temperature sensing means.

10. The ablation catheter as in claim 7, further comprising the material of the electrode being selected from the group of platinum, iridium, gold, silver, stainless steel, and Nitinol.

11. A catheter system comprising:

a catheter shaft having a distal tip section, a distal end, a proximal end, and at least one lumen extending therebetween, wherein the distal tip section has at least a stem supporting mechanism, and wherein the distal end has a fluid venting opening;

a handle attached to the proximal end of the catheter shaft; and at least a rollable electrode disposed at the tip section, wherein said rollable electrode is secured by the stem supporting mechanism.

12. The catheter system as in claim 11, further comprising fluid being supplied to the distal tip section of the catheter shaft and diffused out of the fluid venting opening.

13. The catheter system as in claim 12, wherein the fluid is selected from the group of saline, heparin, antibiotics, chemotherapy and therapeutics fluids.

14. The catheter system as in claim 11, further comprising a steering mechanism at the handle, wherein the steering mechanism provides at least one deflectable curve on the distal tip section of the catheter system.

15. The catheter system as in claim 11, wherein the at least one stem supporting mechanism is located at a side of the catheter shaft of the distal tip section.

16. The catheter system as in claim 12, further comprising RF energy being delivered to the at least one rollable electrode disposed at the distal tip section.

17. The catheter system as in claim 16, further comprising at least one temperature sensing means and a close-loop temperature control mechanism for the catheter system.

18. The catheter system as in claim 11, wherein the rollable electrode is constructed of a porous substrate.

19. The catheter system as in claim 11, further comprising the rollable electrode being selected from the group of roller electrode, wheel electrode, or circular saw electrode.

20. A method for operating a catheter system having a distal tip section with a rollable electrode inside a hollow pocket, within a heart chamber, comprising:

(a) percutaneously introducing the catheter system through a blood vessel to the heart chamber, wherein the distal tip section comprises a rollable electrode;

(b) deflecting the distal tip section of the catheter shaft about a transverse axis to position the electrode near a target on an interior wall of the heart chamber;

(c) intimately contacting the electrode with the intracardiac tissue; and (d) applying RF energy to the rollable electrode for ablation.

* * * * *